United States Patent [19]

Raisanen

[11] 4,165,633
[45] Aug. 28, 1979

[54] SYSTEM FOR MEASURING MOISTURE CONTENT

[75] Inventor: Walfred R. Raisanen, Scottsdale, Ariz.

[73] Assignee: Motorola Process Control Inc., Tempe, Ariz.

[21] Appl. No.: 876,300

[22] Filed: Feb. 9, 1978

[51] Int. Cl.² ........................................... G01N 25/56
[52] U.S. Cl. ..................................................... 73/76
[58] Field of Search ............................................ 73/76

[56] References Cited

U.S. PATENT DOCUMENTS

| | | | |
|---|---|---|---|
| 2,047,765 | 7/1936 | Brabender | 73/76 |
| 2,569,749 | 10/1951 | Dietert et al. | 73/76 |
| 3,909,598 | 9/1975 | Collins et al. | 73/76 |

Primary Examiner—Anthony V. Ciarlante
Attorney, Agent, or Firm—Joe E. Barbee

[57] ABSTRACT

A system for measuring moisture content in a porous material uses a microprocessor. The sample of material is placed on a load cell which provides an output to an analog-to-digital converter. The analog-to-digital converter provides a digital input for the microprocessor. The microprocessor is capable of providing an output indicative of the moisture content as a wet basis or a dry basis output. The system provides a highly accurate measurement of the moisture content while minimizing operator errors.

11 Claims, 4 Drawing Figures

FIG. 4 INTERRUPT ROUTINE

SYSTEM FOR MEASURING MOISTURE CONTENT

BACKGROUND OF THE INVENTION

This invention relates, in general, to measuring change of weight of a material, and more particularly, to thermal gravimetric measurement of moisture content in a porous material.

Determination of moisture content in materials is of such importance in so many fields that a wide variety of devices and analytical methods are used. The traditional method for measuring moisture content in solids and non-volatile liquids is thermal gravimetric. In a thermal gravimetric system a small sample of the material is carefully weighed and then the material is dried by the application of heat thereto and re-weighed after drying. Any difference in weight is indicative of the moisture content. The drying process may be simple exposure to ambient air or in some cases a drying oven may be used. In the past thermal gravimetric measurements were done manually by an operator and were very time consuming and in most cases somewhat inaccurate. More recently, systems have been developed which require fewer operator manipulations but still require periodic operator calibration and adjustments of the measurement system. Such adjustments are not only time consuming but are prone to human error. In view of the foregoing, it should now be understood that it would be desirable to provide an improved thermal gravimetric system that is highly automated, time saving, and highly accurate.

Accordingly, one of the objects of the present invention is to provide a system capable of measuring the moisture content of a material using a microprocessor.

Another object of the present invention is to provide a thermal gravimetric moisture content measurement system capable of providing wet basis or dry basis output information.

A further object of this present invention is to provide a self calibrating weight measuring system.

SUMMARY OF THE INVENTION

In carrying out the above and other objects of the invention in one form, there is provided an improved system for measuring moisture content of a porous material. Means for weighing the material are provided wherein the means for weighing produces an electrical output. Means for heating the material is used to dry out the moisture contained therein. An analog-to-digital converter is used to convert the output of the means for weighing to digital data. Means for processing the digital data is used to determine the weight of the material while it is being dried out and to provide an output indicative of the moisture content of the material. The output of the means for processing is displayed in a format which can be read by an operator. In a preferred form, the system is capable of providing an output indicating wet basis or dry basis moisture content of the material.

The subject matter which is regarded as the invention is set forth in the appended claims. The invention itself, however, together with further objects and advantages thereof, may be better understood by referring to the following detailed description taken in conjunction with the accompanying drawings.

BRIEF DESCRIPTION OF THE DRAWINGS

FIG. 4 is a flowchart indicating the interrupt routine of the system.

The exemplifications set out herein illustrate the preferred embodiment of the invention in one form thereof, and such exemplifications are not to be construed as limiting in any manner.

DESCRIPTION OF THE PREFERRED EMBODIMENTS

Figure 1:
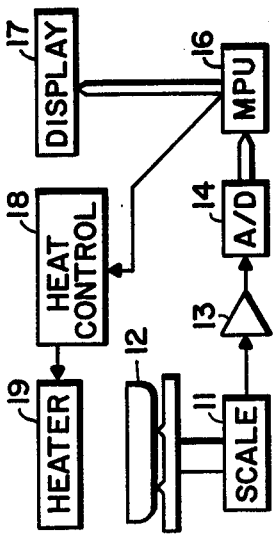
FIG. 1 illustrates a simplified block diagram of the invention.

FIG. 1 illustrates a thermal gravimetric system in simplified block diagram orm. A thermal gravimetric system is used to determine moisture content of a material. The system uses heat to volatize those constituents of a test material that vaporize at temperatures lower than that supplied by the heat. The thermal gravimetric system then utilizes the force of gravity acting upon the changing mass of the test material to produce signals corresponding to the weight of the test material as volatile constituents or elements are driven off by the heat. In the present invention, these signals are converted to digital numbers and stored. An internal xomputer illustrated as microprocessor 16 begins to predict the final mass value when sufficient digital data is available. When the mass value stops changing the computer calculates and displays a number indicating the moisture content of the test material.

To make a measurement of moisture content the test material is placed in pan 12 which is mounted on a scale 11. In a preferred embodiment scale 11 is a load cell of the type sold by Kulite Semiconductor as Model BG-25. This load cell includes a srain gauge bonded to a calibrated beam and provides means for obtaining weight of the test material. The strain gauge provides an electrical output signal which is connected to an amplifier 13 so that the electrical signal can be amplified. The output of the amplifier is coupled to an analog-to-digital converter 14 where the signal is converted to digital data. The digital data is coupled to microprocessor unit 16 where calculations are performed to determine moisture content of the test material. The output of microprocessor 16 is coupled to a display unit 17 where the information is displayed to indicate moisture content of the test sample. The microprocessor 16 is also coupled to heat control unit 18 which in turn drives heater 19. Preferably, heater 19 provides 130° C. of heat to dry out the test material. Thermal gravimetric system 10 is capable of measuring the moisture or volatile contents of a material wherein the volatile contents vaporize at temperatures below 130° C.

Figure 2:
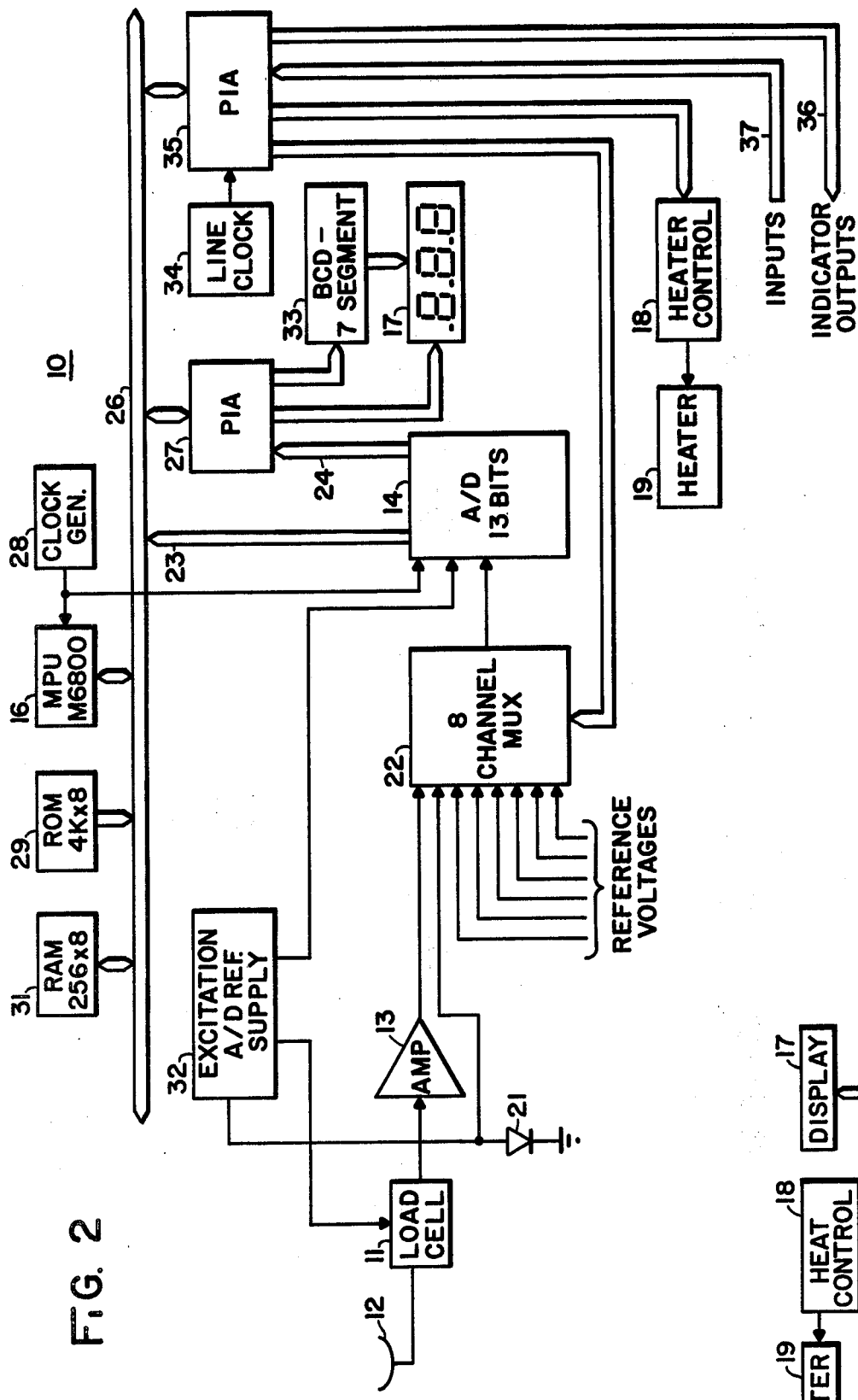
FIG. 2 illustrates the invention of FIG. 1 in greater detail.

Referring now to FIG. 2, thermal gravimetric system 10 is illustrated in greater detail. The output of scale or load cell 11 is connected to amplifier 13. In a preferred embodiment amplifier 13 has a gain of approximately 40 dB and a bandwidth of 1 Hz. The low bandpass reduces errors due to vibrations or other external effects and also allows the amplifier to perform a function similar to a sample and hold circuit. The output of amplifier 13 is connected to a multiplexer 22. Multiplexer 22 is used to permit other signals to be processed by analog-to-digital converter 14. Analog-to-digital converter 14 is a 13-bit converter to provide greater resolution. Converter 14 can be any analog-to-digital converter such as sold by Analog Devices as Part No. AD7550BD. The eight least significant bits of the analog-to-digital converter 14 are connected by line 23 to digital data bus 26. The five most significant bits are connected by line 24 to peripheral interface adaptor 27. The peripheral interface adaptor couples these five bits to digital bus 26 after providing a slight delay to them. Since digital data bus 26 is only capable of handling eight bits the output of the analog-to-digital converter 14 is split up into the two groups. Digital data bus 26 carries the digital data to microprocessor 16. Bus 26 also couples read only memory 29 and random access memory 31 to microprocessor 16. Clock generator 28 generates timing pulses for microprocessor 16 and also provides a timing pulse for analog-to-digital converter 14.

After microprocessor 16 has processed the digital data, the data is coupled by bus 26 to peripheral interface adaptor 27 and peripheral interface adaptor 35. Peripheral interface adaptor 27 provides an output to a circuit 33 which performs a binary coded decimal (BCD) to seven segment conversion. The seven segment converted output is connected to display 17. By way of example, display 17 can be a seven segment light emitting diode (LED) display. Peripheral interface adaptor 27 also provides a display refresh signal directly into display 17.

Peripheral interface adaptor 35 provides eight indicator outputs, and a heater control output, and also receives control inputs for system 10. The heater control output from peripheral interface adaptor 35 is connected to heater control unit 18 which in turn drives heater 19. A suitable heater 19 was found to be a nichrome heating element of the type sold by Thermo Craft Inc. as Part FPH-202. Peripheral interface adaptor 35 receives a start test input which instructs system 10 to commence a moisture content test of a material which will be placed in container 12. System 10 is arranged such that once container 12, which is placed on load cell 11, is loaded a door or cover can be closed over container 12 to reduce effects of air currents around the unit. The door closes on a microswitch which sends a signal into peripheral interface adaptor 35 to indicate that the door has been closed prior to commencement of measurements. Another input into peripheral interface adaptor 35 controls the format (wet basis/dry basis) of the information displayed on display 17. Peripheral interface adaptor 35 also provides eight outputs which can be used to control light indicators which can inform the operator of the different status of the system. As an example, an indicator illuminated by outputs from adaptor 35 may be used to inform the operator that the system is in normal operation, a sequence error has occurred, that more material must be added to container 12, that the test sequence is complete, that some of the material must be removed from container 12 in order to obtain accurate test results, that the indication displayed on display 17 is a preliminary reading, that the indication displayed on display 17 is a final reading, or that a system failure has occurred. Peripheral interface adaptor 35 also provides an output to control multiplexer 22.

One of the inputs to peripheral adaptor 35 controls whether the output displayed on display 17 is a wet basis or dry basis readout. A wet basis readout indicates the percent moisture content of the material under test while a dry basis readout indicates the moisture ratio of the material after it has been dried out. To obtain the wet basis result, the amount of the moisture removed from the sample material is divided by the starting weight of the material. The quotient obtained is multiplied by 100 percent to produce the reading in percentage moisture. To obtain the dry basis answer the amount of moisture removed from the sample material is divided by the weight of the dried out sample. This produces a moisture ratio quotient which can be displayed on display 17.

Heater control unit 18 can maintain heater 19 output to 130° C. plus or minus 3° C. A temperature sensor 21 such as a silicon diode probe can be used to sense the heat produced by heater 19. An output from temperature sensor 21 is connected to multiplexer 22. This output is converted to digital information and acted upon by microprocessor 16 to provide the control to heater controller 18 by way of peripheral interface adaptor 35.

Peripheral interface adaptor also receives an input from line clock generator 34. Line clock generator 34 provides a 120 Hz output which is synchronized to the 60 cycle Hz main power supply. The 120 Hz output from generator 34 is used to provide interrupts to system 10. The purpose of the interrupts is to synchronize the analog-to-digital sampling with the main power supply line voltage. Preferably, the sampling is done at zero crossover of the main power line frequency to minimize errors due to power line transients. In addition, the interrupts can be used to switch multiplexer 22 between outputs from amplifier 13 and temperature sensor 21.

Multiplexer 22 is capable of receiving six reference voltage inputs which can be fixed voltages generated by an internal power supply of system 10 and can be used for diagnostic and calibration purposes by system 10.

A supply 32 is used to generate excitation for the strain gauge used in load cell 11. In addition, supply 32 supplies a current for temperature sensor 21. The system can use one of the reference voltages connected to multiplexer 22 to perform a diagnostics routine to determine whether temperature sensor 21 is operative or not. This is a safety feature to prevent a sample material in container 12 from being overheated should sensor 21 be inoperative. Supply 32 also supplies an analog-to-digital converter reference for analog-to-digital converter 14.

By way of example only, the following parts which are sold by Motorola may be used in system 10. Random access memory 31 can be obtained by using two MC6810 chips. Read only memory 29 can be obtained by using four MC2708 chips. Microprocessor 16 can be an M6800 microprocessor. Peripheral interface adaptors 27 and 35 can be MC6820 chips. Multiplexer 22 can be a standard 508 Multiplexer; one supplier being Siliconix.

Figure 3:
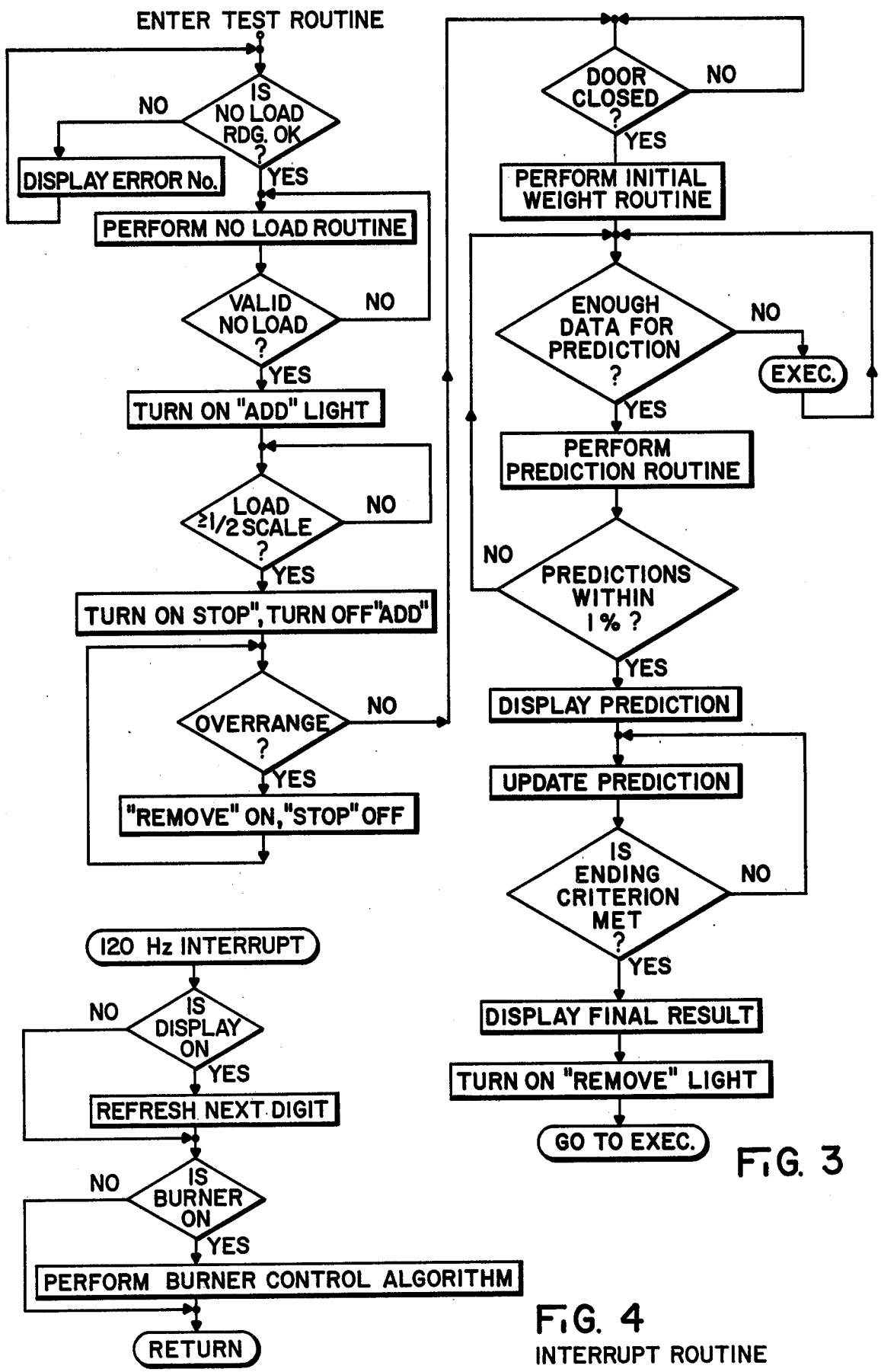
FIG. 3 is a flowchart of a portion of the routine followed in carrying out the invention.

Reference to the program flowchart illustrated in FIG. 3 will help to better understand the operation of thermal gravimetric system 10. The system is capable of measuring the volatile/moisture content of any solid or semi-solid material that is of a porous character. To start a test, an empty container is placed on the load cell and a tare weight reading is obtained. Should the tare weight exceed a predetermined limit a number will be displayed on display 17 to indicate to the operator an improper tare weight. If the tare weight is determined to be of the proper value an indicator light will be illuminated to indicate to the operator that the material desired to be sampled can now be added to the container. A typical sample will consist of from 2 to 5 grams of the material. Once the proper amount of material has been loaded in the container the add light will be turned off and a stop light will be illuminated. If too much material is placed in the container an overrange will occur and an indicator will be illuminated to indicate to the operator to remove material. A door is then closed over the load cell and material and will energize the microswitch as discussed hereinbefore. The material is then weighed to determine the wet or starting weight. As the heater dries out the sample material, data is collected by the microprocessor so that the microprocessor can make an initial calculation of moisture content. This initial indication is displayed on display 17 and an indicator light is illuminated to indicate to the operator that the reading is a preliminary reading. The display on display 17 is continuously updated until no change occurs at which time another indicator is illuminated to indicate that the test is complete. Prior to the preliminary indication being displayed the microprocessor verifies that it is within one percent of a previous reading. This is done to provide an accurate preliminary reading.

FIG. 4 illustrates in program flowchart form how the 120 Hz interrupt generated by clock line generator 34 is used. When an interrupt occurs and the display is "on", the display will be refreshed so that the display will not become so dim that an operator will not be able to read it. Once the refresh is performed, the system verifies that heater 19 is "on" so that the output from temperature sensor 21 can be measured in order to properly control the output heat from heater 19.

By now it should be appreciated that there has been provided a system that combines the simplicity of thermal gravimetric moisture measurement with the sophisticated control and computational power of the microprocessor. The system can accurately and quickly determine the moisture/volatile content of a test sample and display the results in easy to read form. The system substantially eliminates operator error and judgment factors. The system can provide an output reading in wet basis or dry basis form.

Although the system of the present invention has been described as having application to thermal gravimetric moisture content measurements it will be recognized by those persons skilled in the art that the system is useful in determining small rates of change of weight or in obtaining general weight measurements where high accuracy is desired.

Consequently, while in accordance with the Patent Statutes, there has been described what at present is considered to be the preferred forms of the invention. It will be obvious to those skilled in the art that numerous changes and modifications may be made herein without departing from the spirit and scope of the invention, and it is therefore aimed that the following claims cover all such modifications.

What is claimed as new and desired to secure by Letters Patent of the United States is:

1. A gravimetric moisture measuring system, comprising: means for weighing a material whose moisture content is to be determined, the means for weighing producing an output electrical signal representative of weight of the material; an analog-to-digital converter coupled to the means for weighing to provide a digital output representative of the weight of the material; a digital data processor for processing the digital output and for determining change of the digital output to allow the digital data processor to provide a continuously updated output representative of the moisture content of the material, the digital data processor including a microprocessor, a random access memory, and a read only memory; means for displaying the output of the digital data processor; and mean for heating the material to cause a change in the moisture content of the material the means for heating being controlled by the digital data processor.

2. A gravimetric moisture measuring system as recited in claim 1 wherein the means for heating is controlled by the digital data processor, and the means for weighing is a load cell having a strain gauge means for determining weight of the material, and further including a multiplexer coupled to the analog-to-digital converter and having a plurality of reference voltages as inputs.

3. A gravimetric moisture measuring system as recited in claim 1 further including an amplifier coupled between the means for weighing and the analog-to-digital converter and wherein the digital data processor can provide a wet basis and a dry basis output to indicate the moisture content of the material.

4. A thermal gravimetric system for measuring moisture content of a porous material, comprising: means for weighing the material, the means for weighing providing an output corresponding to weight of the material; means for heating the material for a period of time to dry out moisture contained therein; means to convert the output of the means for weighing from an analog signal to digital data; means for processing the digital data in a manner to determine rate of change in the means for processing controlling the period of time the means for heating provides heat to the means to convert and having a plurality of reference voltages coupled to the multiplexer so that the reference voltages can be used for calibration and diagnostic purposes.

5. A thermal gravimetric system as recited in claim 4 wherein the means for weighing uses strain gauges to provide the output.

6. A thermal gravimetric system as recited in claim 5 wherein the means for heating is a nichrome heating element.

7. A thermal gravimetric system as recited in claim 6 wherein the means to convert comprises an amplifier, and an analog-to-digital converter.

8. A thermal gravimetric system as recited in claim 7 wherein the means for processing is a microprocessor and is also capable of controlling the means for heating and capable of providing an output when the material is over a predetermined weight, the means for processing further including a read only memory.

9. A thermal gravimetric system as recited in claim 4 wherein the means for processing can provide an output indicative of wet basis and dry basis moisture content of the porous material.

10. A thermal gravimetric system for measuring moisture content of a porous material, comprising: a scale for measuring the material and for providing an electrical output corresponding to weight of the material; a low bandwidth amplifier coupled to the scale to amplify the electrical output; an analog-to-digital converter coupled to the amplifier for converting the amplified electrical output to a digital signal; a microprocessor for processing the digital signal to provide outputs indicative of moisture content of the material; a read only memory coupled to the microprocessor; a digital data bus for coupling data to the microprocessor; a peripheral interface adaptor coupled to the data bus for coupling a portion of data from the analog-to-digital converter to the microprocessor; an alpha-numeric display coupled to the peripheral interface adaptor to display outputs of the microprocessor; and a heating element to heat the material to dry out moisture contained therein, the heating element being coupled to the digital data bus so that the microprocessor can control how long a period of time the heating element provides heat.

11. The thermal gravimetric system of claim 10 wherein the moisture content of the material can be displayed as dry basis and wet basis.

* * * * *